United States Patent [19]

Collet-Cassart et al.

[11] Patent Number: 4,556,642
[45] Date of Patent: Dec. 3, 1985

[54] PARTICLE AGGLUTINATION ASSAY OF ANTIGENS

[75] Inventors: Daniel Collet-Cassart, Kraainem; Jean-Claude Mareschal, Malonne; Pierre L. Masson, Brussels, all of Belgium

[73] Assignee: International Institute of Cellular & Molecular Pathology, Brussels, Belgium

[21] Appl. No.: 520,288

[22] Filed: Aug. 4, 1983

[30] Foreign Application Priority Data

Aug. 6, 1982 [GB] United Kingdom ............... 8222776

[51] Int. Cl.$^4$ .................. G01N 33/54; G01N 33/68; G01N 33/74
[52] U.S. Cl. .................................. 436/500; 436/510; 436/512; 436/534; 436/811; 436/814; 436/815; 436/817; 436/823; 436/825
[58] Field of Search ............... 436/501, 503, 512, 500, 436/518–520, 528–534, 534 EP, 536, 537, 811, 814, 815, 817, 825, 510; 435/7

[56] References Cited

U.S. PATENT DOCUMENTS

| | | | |
|---|---|---|---|
| 4,205,954 | 6/1980 | Babson | 250/574 |
| 4,305,925 | 12/1981 | Kapmeyer et al. | 356/339 |
| 4,329,152 | 5/1982 | Lauwerys et al. | 436/534 |
| 4,419,453 | 12/1983 | Dorman et al. | 436/534 |
| 4,427,781 | 1/1984 | Masson et al. | 436/509 |
| 4,455,381 | 6/1984 | Magnusson et al. | 436/543 |

FOREIGN PATENT DOCUMENTS

EP038181 10/1981 European Pat. Off. .
EP051985 5/1982 European Pat. Off. .
EP083869 7/1983 European Pat. Off. .
EP101228 2/1984 European Pat. Off. .

OTHER PUBLICATIONS

J. Clin. Chem. Clin. Bioc., vol. 20(3), pp. 141–146, (1982), Timet, J. et al.
Methods in Enzymology, vol. 74, pp. 106–139, (1981), Masson, P. L. et al.
Magnusson, C. G. M. et al, Clin. Allergy, vol. 11 (5), pp. 453–461, (1981).
Masson, P. L. et al, Immunoassays 80s, pp. 35–41, (1981).
Collet-Cassart, D. et al, Clin. Chem., vol. 29(6), pp. 1127–1131, (1983).
Timet, J. N. et al., J. Immunol. Methods, vol. 28, (1-2), pp. 25–32, (1979).
Sindie, C. J. et al, Molecular Immunology, vol. 18(4), pp. 293–299, (1981).
Cambiaso, C. L. et al, J. Immunolog. Methods, vol. 23(1-2), pp. 29–50, (1978).
Cambiaso, C. L. et al, J. Immunol. Methods, vol. 18(1-2), pp. 33–44, (1977).
Voller, A., RIA-Related Proced. Med., pp. 723–733, (1982).

Primary Examiner—Thomas G. Wiseman
Assistant Examiner—M. Moskowitz
Attorney, Agent, or Firm—E. H. Gorman, Jr.

[57] ABSTRACT

In a particle agglutination assay for an antigen (Ag), there is included in the mixture a limited amount of a substance which binds univalently with a proportion of the Ag present, that Ag which is so bound being unable then to cause agglutination of the particles. In this way, unusually large concentrations of Ag can be assayed in that a proportion of the Ag is bound to the univalent substance and the particle agglutination assay is in effect conducted on the smaller amount of Ag still remaining free in solution.

7 Claims, 1 Drawing Figure

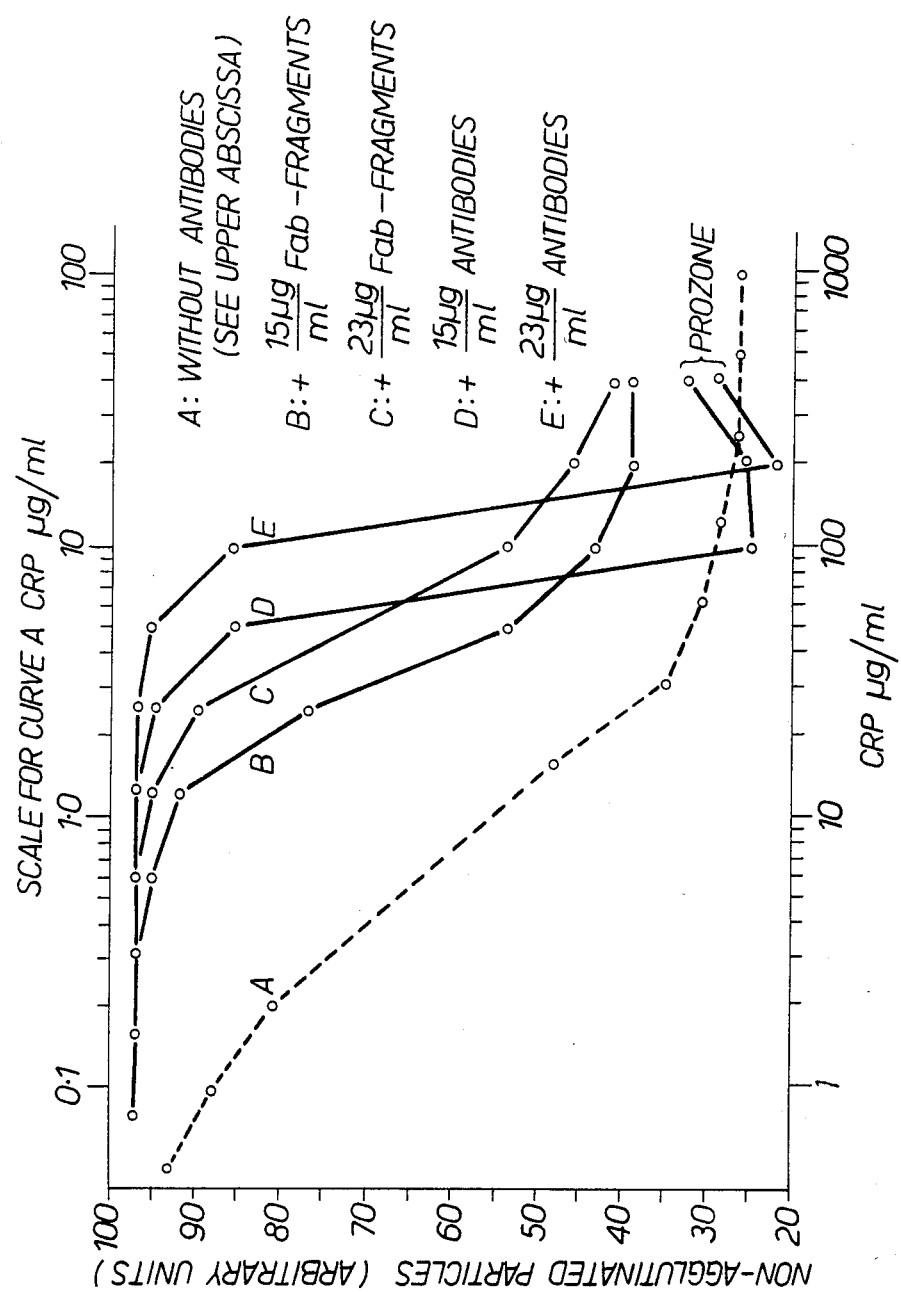

PARTICLE AGGLUTINATION ASSAY OF ANTIGENS

BACKGROUND OF THE INVENTION

This invention relates to the immunoassay of antigens (Ag), and more particularly to the immunoassay of Ag by a particle agglutination technique.

BRIEF DESCRIPTION OF THE PRIOR ART

Particle agglutination immunoassays have been known for many years. Broadly, they consist in forming a suspension of finely divided particles in a fluid, the particles bearing a reagent, and causing the particles to agglutinate in response to the presence of an analyte, the degree of agglutination providing a measure of the amount of analyte present. Ag can be assayed in this way, by using an antibody (against the Ag) as the reagent on the particles, the Ag (analyte) directly causing agglutination of the particles, i.e. the Ag acts as an agglutinator. For various known reasons, it is preferred to determine the degree of agglutination (and hence the amount of Ag present) by counting the number of particles remaining unagglutinated.

In practice, such assays are effected by firstly establishing a standard curve (or set of standard results) relating the particle count to the amount of Ag present, using standard conditions. The sample containing an unknown amount of Ag is then assayed under the same conditions and, from the particle count obtained and the standard curve, the amount of Ag is determined.

BRIEF DESCRIPTION OF THE DRAWING

In order that the present invention may be more fully understood, reference will hereafter be made to FIG. 1 which shows five standard curves, labelled A to E, for a particle agglutination assay of C-reactive protein (CRP). The ordinate shows the number of unagglutinated particles, the upper abscissa relates only to curve A, and the lower abscissa relates to curves B to E. In both cases, the abscissa show the concentration of CRP in $\mu g/ml$.

DESCRIPTION OF THE PRIOR ART

Referring to FIG. 1, standard curve A relates (upper abscissa) the concentration of an Ag (CRP) with the number of unagglutinated particles (ordinate). It can be seen that this curve is appropriate for determining amounts of Ag from about 0.1 to 50 $\mu g/ml$. At concentrations greater than about 50 $\mu g/ml$ of Ag, the curve is too flat to give accurate results. The general shape of curve A is typical although, as will be appreciated, the concentration range over which a curve can be used for any particular Ag will vary with the Ag and the conditions used. It remains the case, however, that under any set of conditions, the standard curve will be sensitive only for a limited concentration range of the Ag.

In practice, for many Ag, the sensitivity range of the assay method under any particular conditions presents no problem since the Ag very rarely has to be assayed at concentrations outside this range. For some Ag, however, the limited sensitivity range does provide a problem, because the range does not cover all concentrations at which the Ag might reasonably be expected to be present in, for example, human serum. C-reactive protein (CRP) is an example. Its concentration in human serum in healthy individuals is normally less than 1 $\mu g/ml$ and hence curve A is appropriate. However, in patients suffering an acute inflammation, the CRP concentration can be as high as 1000 $\mu g/ml$ (i.e. 1 g/liter), and at such concentrations, curve A is not useful. As a general matter, rather than establish another standard curve under different conditions whereby larger concentrations of Ag can be measured, it is preferable to dilute the "concentrated" Ag sample to bring its Ag content within the sensitivity range of the established standard curve.

Particle agglutination assays for Ag can, of course, be conducted manually in which case a dilution step can be effected relatively simply. It is preferred, however, to conduct such assays on an automated system, such as that known as PACIA and described in, for example, Clinical Allergy, 1981, Volume 11, pages 453–461. In this system and indeed generally in automated systems, only a limited amount of sample dilution can be conveniently achieved, for example a dilution of about 1:50, greater dilutions being more difficult and usually requiring manual intervention. In the assay of CRP described above, a dilution of 1:100 may be necessary to locate the concentration of analyte within the sensitive range of the calibration curve, which presents problems in an automated system. Hence, samples which fall outside of the sensitive range afforded by such automated systems cannot be assayed.

In order to avoid the necessity for large dilutions, it has been proposed instead to add to the sample under assay a limited quantity of soluble antibody to the Ag. In this way, a proportion of the total Ag becomes bound to the soluble antibody, the remaining Ag being free to agglutinate the finely divided particles. Routine trial and experiment will reveal, in any particular case, how much soluble antibody is needed to reduce the concentration of free Ag to within the sensitivity range of the standard curve. An example of this procedure is described by Leek et al., Journal of Automatic Chemistry, Vol. 2, No. 3, July 1980, where, in the assay of human placental lactogen (HPL) by PACIA, free soluble anti-HPL was added to decrease the sensitivity to within the standard curve range. Since soluble antibody is divalent, it functions not only to reduce total antigenic determinants, but also to aggregate the HPL which is also multivalent. In addition to the use of soluble antibody, dilution was also used by Leek et al, and it was found that no loss of precision or accuracy in the overall assay was thereby introduced.

Whilst this technique was advantageously employed by Leek et al. as described, its general applicability has certain limitations. In particular it reduces the range of sensitivity of the assay and also tends to promote the appearance of the so-called "prozone effect" due to the use of the divalent soluble antibody, as described above. The prozone effect manifests itself in that, above a certain concentration of Ag (or, more generally any agglutinator), the amount of agglutination decreases rather than increases. In FIG. 1, curves D and E are standard curves for a particle agglutination assay of CRP in which, in curve E, 23 $\mu g/ml$ anti-CRP soluble antibodies were added and, in curve D 15 $\mu g/ml$ of the antibodies were added. The two limitations referred to above are evident in both curves, viz. the range of sensitivity is in both cases (lower abscissa) less than for curve A, and both curves D and E exhibit the prozone effect.

We have now found that both these limitations can be avoided if, instead of using soluble whole antibodies to decrease the sensitivity, there is used instead a substance which is univalent towards the Ag under assay and binds with a proportion of the Ag present and thereby prevents that proportion agglutinating the particles. In this way, the range of sensitivity is not significantly altered, and the prozone effect does not appear.

According to the present invention, therefore, there is provided a particle agglutination immunoassay for an Ag in a liquid sample, wherein there is included in solution in the assay mixture a substance which is univalent towards the Ag and is capable of binding therewith, the Ag so bound being unable to agglutinate the particles.

The invention further provides a method of assaying an Ag in a sample by a particle agglutination assay, in which the sample is mixed with a suspension of unagglutinated finely divided particles bearing a reagent which binds with the Ag to cause agglutination of the particles, the amount of Ag being determined by measuring the extent of agglutination and referring to standard results obtained by measuring the extent of agglutination with a range of known amounts of Ag, the improvement whereby amounts of Ag greater than said range can be assayed, which improvement comprises (a) establishing new standard results for an assay in which there is also included in the mixture a known quantity of a substance which is univalent towards the Ag and is capable of binding therewith so that Ag so bound is not able to agglutinate the particles, said quantity of substance being insufficient to bind with all the Ag under assay; and (b) conducting said assay, using said known quantity of substance, on said sample of Ag and determining from the extent of agglutination and the said new standard results, the amount of Ag in the sample.

A particularly preferred univalent substance is one formed by modifying whole antibody to render it univalent towards the Ag. We prefer to effect such a modification by enzymatically digesting the antibody. For example, the enzyme papain may be used to form monovalent F(ab) fragments of the antibody. When the enzyme pepsin is used, bivalent F(ab')$_2$ fragments are produced and these are then reduced and alkylated to render the monovalent. Such procedures are known in the art.

Alternatively, it may be possible with certain Ag to use whole antibodies thereto which are monovalent towards the Ag. For example, the so-called "hybrid antibodies" could be used. These are obtain by preparing first half molecules of antibodies by selective reduction of the disulfide bonds joining the heavy chains, followed by acidification. Half molecules recombine spontaneously at neutral pH through non-covalent forces; therefore, they remain as half molecules (monovalent) only under dissociating conditions, such as low pH or the presence of detergents. If the dissociation of a given set of antibodies occurs in the presence of antibodies with another specificity, the reassociation of the half-molecules after neutralisation of pH can occur at random and hybrid antibodies will be formed. These antibodies with two different specificities are monovalent in respect of each specificity.

In the particle agglutination assay of the invention, the finely-divided particles (normally so-called latex particles of size of the order of 1 micron) bear a reagent which binds to the Ag to result in particle agglutination. Usually, the reagent will be an antibody raised against the Ag, although other binding substances may be used. As described in U.S. Pat. No. 4,397,960, we prefer to use as the reagent on the particles, the F(ab')$_2$ fragments of an antibody (rather than whole antibody) since this reduces the effect of various interferences, such as RF and Clq, in the assay.

Also, interference in the assay can be further reduced by the use of chaotropic agents, as in U.S. Pat. No. 4,362,531, to block the binding of serum proteins to the latex particles or by the techniques described in U.S. Ser. No. 06/452,180, which teaches the addition of non-specific F(ab')$_2$ fragments to block interspecies crossactivity.

The amount of univalent substance used in the method of the invention will be insufficient to bind with all the Ag under assay. Routine trial and experiment in any particular case will reveal the optimum quantity to be used, which will in general be such as to leave free in solution an amount of Ag falling within the sensitivity range of the assay method. In determining (at the end of the assay) the quantity of Ag in the original sample, account will of course be taken of the effect of adding the univalent substance.

The method of the invention is particularly, but not exclusively, useful in the assay of an Ag sample in which the concentration of Ag is greater than or equal to the maximum which can be accurately determined in the assay system. Whilst there is no limitation on the type of Ag which may be assayed (except that it may not be monovalent, i.e. a hapten), the method is particularly useful in the assay of CRP, thyroxin-binding globulin (TBG), HPL, prealbumin, the pregnancy protein called SP1, and generally for serum proteins.

It should be noted that, in the assay of Ag which are proteins (e.g. antibodies), the whole protein may first be digested to form a fragment which maintains its specific antigenicity and which is then assayed, the other interfering proteins having been degraded, as described in U.S. Pat. No. 4,455,381.

The method of the invention is particularly useful in automated systems, such as PACIA, but can also of course be used in manual assays.

In order that the invention may be more fully understood, the following Example is given by way of illustration only.

EXAMPLE

Assay of CRP (a) IgG antibodies were raised against CRP and the F(ab) fragments thereof were prepared as follows. A solution of 10 mg/ml antibodies in 0.1M phosphate buffer, pH 7, containing 0.01M cysteine and 0.002M ethylenediamine tetra-acetic, was incubated with papain at an enzyme/protein ratio of 1/100 for 20 hours at 37° C. The F(ab) fragments formed were then recovered by dialysis against physiological saline.

(b) Latex particles were coated with F(ab')$_2$ fragments of anti-CRP antibodies.

(c) The assay was effected by the PACIA system referred to above (see also, for example, Clinical Chemistry, 27, 64 (1981)). Incubation was effected at 37° C. for 25 minutes. A series of samples (30 μl), each containing different amounts of CRP, were mixed with 30 μl of the F(ab) fragment solution in 0.1M glycine buffer, pH 9.2, containing 0.17M NaCl. Two standard curves were produced, as shown in the accompanying drawing, curves B and C (lower abscissa). Curve B was obtained using 15 μg/ml of F(ab) fragments, and curve C using 23 μg/ml of F(ab) fragments.

The curves illustrate two very important advantages of the invention, both of which are unexpected and surprising. Firstly, the shapes of curves B and C (according to the invention) are generally similar to those of D and E, but the useful ranges are greater. Thus, in B the useful range is 3 to 200 μg/ml where as in D, the useful range is only 10 to 100 μg/ml. Similarly, in C the useful range is 6 to 400 μg/ml whereas in D it is only 50 to 200 μg/ml.

Secondly, the prozone effect is shifted to substantially higher concentrations for curves B and C (of the invention) than for curves D and E (prior art).

We claim:

1. In a particle agglutination assay for an antigen (Ag) in a liquid sample, which comprises the steps of forming a reaction mixture of the liquid sample and finely divided particles bearing a reagent, the reagent being such as to bind with the Ag to cause agglutination of the particles; and measuring the extent of agglutination of the particles and therefrom determining the amount of Ag present;

the improvement comprising introducing in solution in the reaction mixture a predetermined sensitivity increasing amount of a substance which is univalent towards the Ag and which specifically binds therewith so that the Ag bound to the substance is unable to agglutinate the particles, the quantity of substance being insufficient to bind with all the Ag under assay, and wherein the amount of Ag is determined from the extent of agglutination and the quantity of substance used.

2. A method according to claim 1, wherein the univalent substance is derived from whole antibody which specifically binds to the Ag under assay.

3. A method according to claim 2, wherein the univalent substance is a fragment of said whole antibody which is univalent to and specifically binds to the Ag.

4. A method according to claim 2, wherein the univalent substance is a hybrid antibody which is univalent to and specifically binds to the Ag.

5. A method according to claim 1, wherein the reagent is whole antibody, or $F(ab')_2$ fragments of whole anitbody, and specifically binds to the Ag.

6. In a method of assaying an Ag in a sample by a particle agglutination assay, in which the sample is mixed with a suspension of unagglutinated finely divided particles bearing a reagent which binds with the Ag to cause agglutination of the particles, the amount of Ag being determined by measuring the extent of agglutination and referring to standard results obtained by measuring the extent of agglutination with a range of known amounts of Ag, the improvement whereby amounts of Ag greater than said range can be assayed, which improvement comprises (a) establishing new standard results for an assay in which there is also included in the mixture a known quantity of a substance which is univalent towards the Ag and is capable of binding therewith so that Ag so bound is not able to agglutinate the particles, said quantity of substance being insufficient to bind with all the Ag under assay; and (b) conducting said assay, using said known quantity of substance, on said sample of Ag and determining from the extent of agglutination and the said new standard results, the amount of Ag in the sample.

7. In a particle agglutination assay for an antigen (Ag) in a liquid sample, which comprises forming a reaction mixture of the liquid sample and finely divided particles bearing a reagent, the reagent being such as to bind with the Ag to cause agglutination of the particles, said Ag being of the group consisting of C-reactive protein, thyroxin binding globulin, human placental lactogen, prealbumin or pregnancy protein SP1; and measuring the extent of agglutination of the particles and therefrom determining the amount of Ag present;

the improvement comprising introducing in solution in the reaction mixture a predetermined sensitivity increasing amount of a fragment of whole antibody which is univalent towards and is derived from whole antibody which specifically binds to the Ag, the antibody fragment binding to the Ag so that the Ag so bound is unable to agglutinate the particles, the quantity of substance being insufficient to bind with all the Ag under assay, and wherein the amount of Ag is determined from the extent of agglutination and the quantity of substance used.

* * * * *